United States Patent [19]

Mendenko et al.

[11] Patent Number: 4,849,645
[45] Date of Patent: Jul. 18, 1989

[54] SUBSTRATE INSPECTION SYSTEM HAVING TWO SCATTERED LIGHT DETECTING BUNDLES ORTHOGONALLY POSITIONED TO EACH OTHER

[75] Inventors: Barry J. Mendenko, Robinsville, N.J.; Bruce M. Nyman, Langhorne, Pa.

[73] Assignee: American Telephone and Telegraph Company, N.Y.

[21] Appl. No.: 164,351

[22] Filed: Mar. 4, 1988

[51] Int. Cl.[4] .................. H01J 5/16; G01N 21/88
[52] U.S. Cl. .................. 250/563; 250/227; 250/572
[58] Field of Search .............. 250/234, 235, 236, 562, 250/563, 571, 572, 227; 356/430, 431, 444; 358/293

[56] References Cited

U.S. PATENT DOCUMENTS 4,317,633 3/1982 Kobayashi et al. .............. 356/430
4,363,118 12/1982 Roach et al. .................. 250/572
4,568,835 2/1986 Imamura et al. ................ 250/572

Primary Examiner—David C. Nelms
Assistant Examiner—William Oen
Attorney, Agent, or Firm—Roderick B. Anderson

[57] ABSTRACT

Surface defects on a substrate (11) are detected by raster scanning the surface (10) with a laser beam (12). Light scattered by the substrate at a large angle with respect to a normal to the surface is collected by at least two bundles of light guide fibers (21,22) located nearly in the plane of the substrate surface, one fiber bundle parallel to the laser scan with the other positioned perpendicularly thereto. The light collected by each bundle is separately processed by a computer (20) to determine the size, in three dimensions, and orientation of defects on the substrate surface. In a preferred embodiment, four light guide fiber bundles (31,32,33 and 34) are used around the substrate surface with the outputs being separately processed.

16 Claims, 4 Drawing Sheets

SUBSTRATE INSPECTION SYSTEM HAVING TWO SCATTERED LIGHT DETECTING BUNDLES ORTHOGONALLY POSITIONED TO EACH OTHER

TECHNICAL FIELD

This invention relates to methods for inspecting flat surfaces, and more particularly, to methods for detecting defects on a flat surface by scanning the surface with a laser beam and detecting light scattered at a large angle with respect to a normal to the surface.

BACKGROUND OF THE INVENTION

U.S. Pat. No. of Jablonowski, 4,286,293 issued Aug. 25, 1981 (assigned to a subsidiary of the present assignee company) is directed to a method for inspecting gold conductors on ceramic substrates by scanning the substrate surface with a laser beam and detecting light reflected and scattered from the surface for display on a video monitor. It was noted that light from the gold conductors was reflected at a relatively small angle with respect to a normal to the surface while light scattered from the ceramic surface was predominantly scattered at a high angle with respect to the surface normal. The patent teaches that greater contrast on the video display between the gold conductors and the ceramic substrates can therefore be obtained by subtracting the light scattered at a high angle from the light received at a relatively low angle to the normal. Thus, the patent teaches the use of two optical fiber waveguides for directing light to two detectors and combining subtractively the detector outputs.

The U.S. Pat. No. of Heebner et al. 4,441,124, issued Apr. 3, 1984 (issued to a subsidiary of the present assignee company) teaches how the principles of the Jablonowski patent can be used for silicon wafer inspection, particularly for detecting the presence of spurious particulates. For this purpose, the light which is displayed on a monitor is that which is scattered at a high angle with respect to the wafer surface normal. To efficiently gather this light, a ring defined by the ends of light guides or optical fibers is arranged around the periphery of the wafer to be inspected. The presence of a particulate is then manifested by an increase of scattered light detected by these optical fibers arranged essentially coplanar with the surface of the wafer (i.e., at a high angle of nearly 90 degrees with respect to the wafer surface normal). In order to provide greater contrast for the display, light scattered and reflected at a relatively low angle with respect to the surface normal is also detected and may be subtracted from the signal generated by the light scattered at a high angle with respect to the normal. Thus, to emphasize light scattered at a high angle with respect to the surface normal, Heebner teaches subtracting light scattered at a low angle; whereas, in Jablonowski, to emphasize light scattered at a low angle, light scattered at a high angle is subtracted.

In adapting the Heebner technique to the inspection of alumina substrates, we have determined that enhancing contrast through a subtraction of light reflected at a low angle is not necessary. However, we have also determined that there is a need to define more accurately the nature of any defects on the surface of alumina substrates being inspected. Specifically, it would be useful to be able to define with some accuracy the dimensions of any defect detected and its topography.

SUMMARY OF THE INVENTION

In accordance with the invention, these objectives are attained, in a method for inspecting surfaces using a scanning laser beam, by collecting light scattered from the surface by two arrays of optical fibers located nearly in the plane of the surface, one array being parallel to the direction of the laser scan and the other positioned perpendicularly thereto. Each of the two arrays is connected to a separate light detector for generating information that is processed separately from the information generated by the other array of optical fibers.

As with the Heebner method, the signals generated are compared with information stored in the computer describing the scattered light that would be expected from a defect-free surface. By arranging the fibers along two separate dimensions, however, one can obtain more accurate information in two dimensions of any defect encountered by the scanning beam. For example, if the defect has a length dimension parallel to the direction of the beam scan, that length will be accurately detected by the optical fibers arranged perpendicularly with respect to the direction of the beam scan, while the width dimension of the defect will be accurately recorded by the fiber array arranged parallel to with the direction of the beam scan.

Measurement in the third dimension, and even more accuracy in the other two dimensions, can be obtained by using four separate arrays of fibers surrounding the periphery of the surface to be inspected, each array being connected to a separate detector which is separately processed by the computer. Thus, for inspecting a typical substrate having four sides, one array is arranged along each of the four sides. This permits accurate detection of light scattered in any of four directions from a defect, thus permitting more accurate mapping by the computer of the geometry of the defect. Each of the four channels are of course separately processed by the computer with information received being compared with stored information, the comparison being used to generate information describing the nature of the defect.

Separate processing of the information from the arrays should not be confused with separate processing of light scattered at a small angle and light scattered at a large angle with respect to the normal as in the Jablonowski or Heebner patents for the purpose of obtaining greater contrast. All of the light gathered by the fiber optic arrays of our invention is light scattered at a relatively large angle with respect to a normal of the surface. If it were desired to collect light scattered at a small angle with respect to the normal for the purpose of providing greater contrast in the manner described by Heebner and Jablonowski, that could also be done; but, as mentioned before, we have found that for alumina substrate inspection, it is not always necessary.

Another advantage of the invention as described is that the computer can be easily programmed to distinguish pit defects (i.e., depressions in the surface) from burr defects (i.e., protuberances from the surface). As will become more clear from the Detailed Description, a pit that is initially encountered by the scanning laser beam tends first to scatter light in the direction of the scan, while a burr tends initially to scatter light in a direction opposite the direction of the scan. With appropriate stored information, the video display can then display the defect as a pit or burr in addition to displaying its dimensions. Additionally, in the inspection of alumina substrates, pits can be discriminated from burrs by comparing the Fourier frequency components of the scattered light pulses with stored information; as will be explained, a relatively low frequency content indicates pits, and a relatively high frequency content indicates burrs.

These and other objects, features and advantages of the invention will be better understood from the following Detailed Description taken in conjunction with the accompanying drawing description.

Drawing Description

Detailed Description

Figure 1:
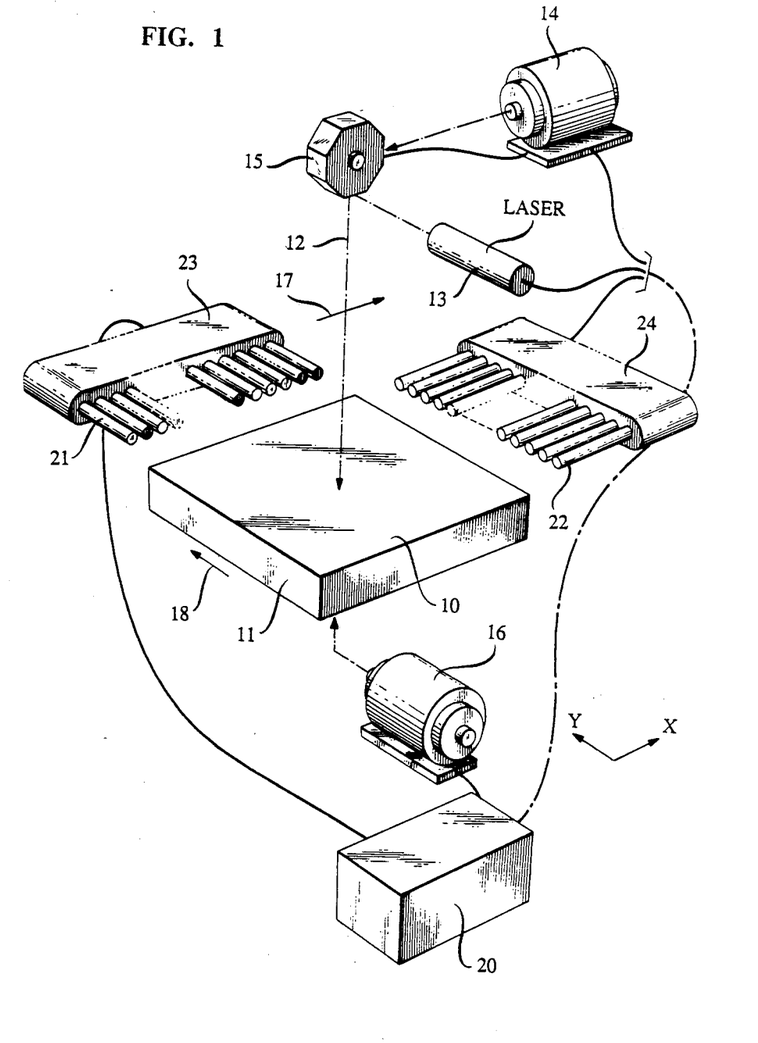
FIG. 1 is a schematic representation of a method for inspecting flat surfaces in accordance with an illustrative embodiment of the invention.

Referring now to FIG. 1, there is illustrated a method for inspecting the flat upper surface 10 of an article 11 to determine the presence of defects, particulates and other departures from surface flatness. a laser beam 12 from a laser 13 raster scans the surface 10. Raster scanning may be accomplished in a known manner by using a motor 14 to drive a rotating mirror 15 and another motor 16 to drive a stage supporting the article 11. The rotating mirror from which the laser beam 12 is reflected causes the beam to scan the surface in an x direction as shown by arrow 17 while the motor 16 slowly moves or steps the article 11 in a y direction as shown by arrow 18. For each x direction scan by the laser beam, the article should be moved in the y direction a distance approximately equal to (1/e) times the diameter of the laser beam. The laser 13 and motors 14 and 16 are controlled and synchronized by a computer 20.

As is known, defects on flat surfaces such as silicon wafers and ceramic substrates are best determined by selectively gathering light scattered at a high angle with respect to the normal to the surface. For this purpose, arrays of optical fibers 21 and 22 are arranged along two sides of the article 11 nearly coplanar with the surface 10. For most purposes, the angle between the optical fibers and a normal to the surface 10 should be greater than 80 degrees but less than 90 degrees; that is, it should be located just slightly above the surface 10 and preferably at nearly 90 degrees to the surface normal. Each time the scanning laser beam 12 encounters a defect on surface 10, light scattered at a high angle with respect to the surface normal is received by optical fibers 21 and 22 and is converted to an electrical signal by light detectors 23 and 24. These signals are directed to the computer 20 where they are combined with information giving the location of the laser beam 12 on the surface 10. This information is used to give an indication of the location of the defect which may be displayed on a video monitor if desired.

In accordance with one embodiment of the invention, the outputs of detectors 23 and 24 are separately processed by computer 20 to give a more dependable description in two dimensions of the defect. That is, the outputs of the detectors 23 and 24 are separately compared with stored information in the computer that discriminates between light scattered from a defect and that scattered from a surface that is flat within predetermined limits, and because the optical fibers are arranged in a specific direction, they can give better directionoriented information. This can be appreciated from a consideration of FIG. 2, which shows illustratively a burr defect 25 having a length in the x direction and shorter width in the y direction. It can be appreciated that when the laser beam scans the surface in the x direction at the position 26, it scatters light predominantly toward optical fibers 21 that are connected to detector 23 of FIG. 1. Thus, it is quite convenient to compare the output of detector 23 with stored information in the computer concerning the scattered light that would indicate a defect and use this comparison information to indicate the length in the x direction of the defect 25. Likewise, when the scanning laser beam is at position 27, light is scattered predominantly toward optical fibers 22, which are connected to detector 24 of FIG. 1. The computer is therefore programmed to compare the output of detector 24 with stored information so as to give information concerning the dimension in the y direction of any defect encountered. Experiment has shown that much more accurate information can be gathered and displayed in this manner than having all of the optical fibers connected to a single detector as is true in the Heebner patent.

Figure 3:
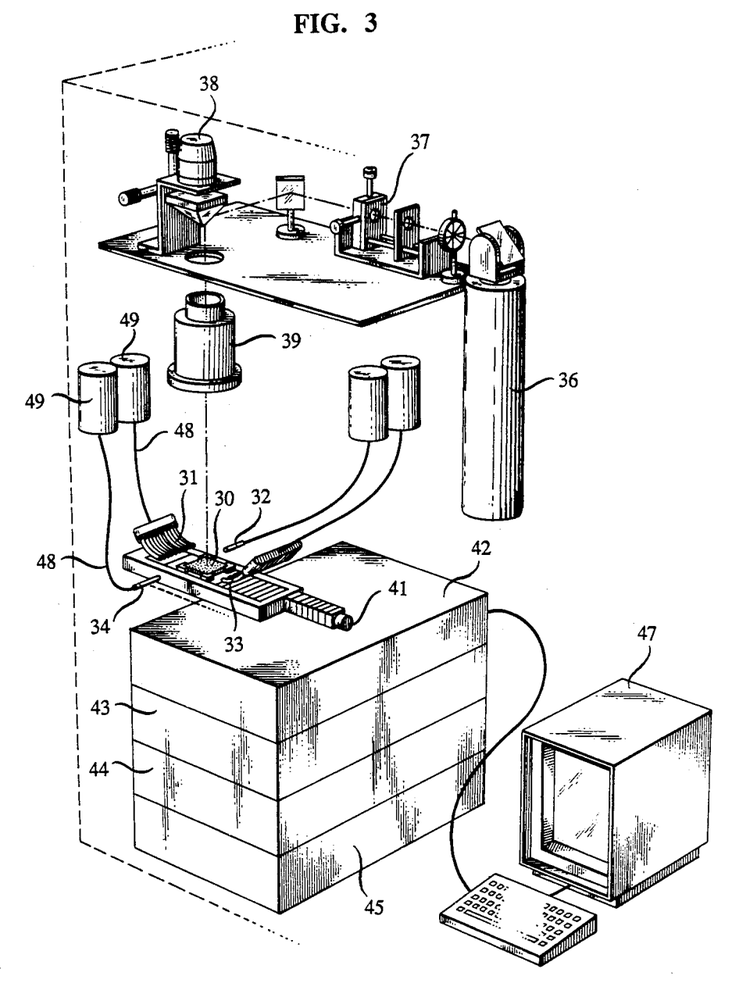
FIG. 3 is a schematic representation of apparatus that has been made and used for practicing the method of FIG. 1.

While the simplest embodiment of the invention makes use of two arrays of optical fibers, more accurate determinations and mapping of threedimensional characteristics of defects can be made by using four separate arrays surrounding the flat surface to be inspected. FIG. 3 is a simplified schematic drawing of such a system that has been built and demonstrated by us particularly for the purpose of inspecting the flat upper surfaces of alumina ceramic substrates. A ceramic substrate 30 to be inspected is surrounded by four separate arrays of optical fibers 31, 32, 33 and 34. While, for purposes of clarity, only one optical fiber of each of the arrays 32 and 34 is shown, it is to be understood that each array is coextensive with one side of the substrate 30. The surface of the ceramic substrate is scanned by a laser beam generated by a 16 milliwatt helium-neon laser 36. The laser beam is directed through a beam expander 37 to a rotating polygon mirror 38, and then through a telecentric scanning lens 39 to the substrate surface. The rotating polygon mirror 38 gives raster scanning in the x direction while a motorized stage 41 supporting the ceramic substrate gives continuous movement in the y direction. The (1/e) diameter of the impinging beam is 25 microns, and the stage advances 25 microns during each raster scan. Arranged on a rack as shown are a computer 42, power supplies 43, electronic circuitry 44 and stage controller 45. The computer is connected to a keyboard and monitor 47 on which a visual display of defect locations and geometries can be made. Each of the optical fiber arrays is connected by an optical fiber bundle 48 to a photomultiplier tube 49. Each of the photomultiplier tubes independently generates a signal dependent on light gathered by one of the fiber optic arrays and transmits the signal to the computer 42 (interconnection not shown).

Figure 2:
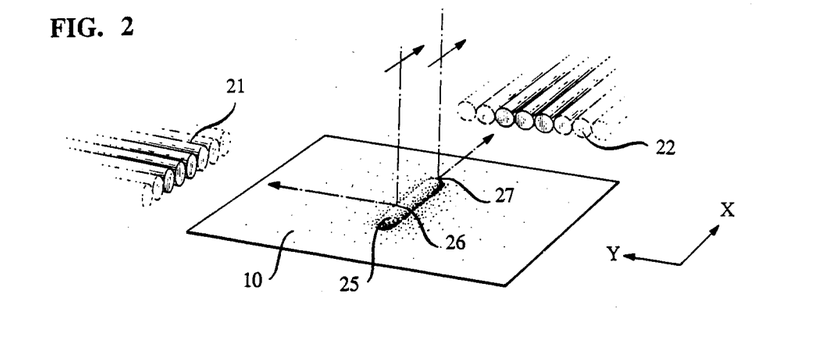
FIG. 2 is a schematic representation illustrating certain light beam scattering in the method of FIG. 1.

One can appreciate from FIG. 2 the advantage of having four rather than only two arrays of optical fibers; light may be scatteredby scattered by burr 25 in the y direction away from fibers 21, and it may be scattered in the x direction opposite fibers 22. Fibers for collecting such light will contribute to output accuracy.

Figure 4:
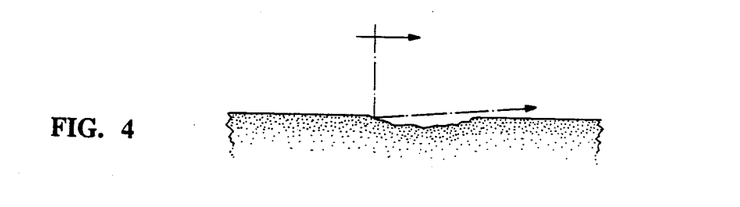
FIGS. 4 and 5 illustrate scanned laser beam scattering caused by different kinds of defects on a flat surface.
Figure 5:
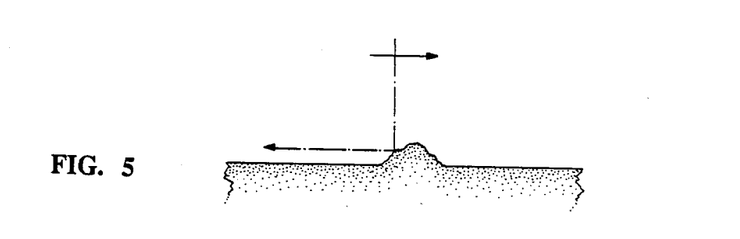

Another advantage of having four arrays of optical fibers can be appreciated from FIGS. 4 and 5. FIG. 4 illustrates that when a scanning laser beam first encounters a pit, light is initially scattered in the direction of scan. Conversely, FIG. 5 illustrates that when a scanning laser beam first encounters a burr, it scatters light predominantly in a direction opposite that of the laser beam scan. Thus, the computer can be programmed with appropriate statistical information so that a distinction can be made between pits and burrs. The appropriate comparisons are of course possible because each of the four arrays of optical fibers are connected to a separate detector, the output of which is separately processed by the computer.

We have found that a further distinction between pits and burrs on alumina substrates can be made by assessing the Fourier components of the light pulse created by the defect. A burr defect is characteristically sharper in geometry than a pit; that is, it characteristically has a steeper slope with respect to the surface. As a consequence, the light pulse created by a burr has steeper slopes and therefore a higher proportion of high frequency components than a pit. Thus, frequency analysis can easily be employed by the apparatus to indicate the nature of the defect, with a high proportion of high frequency components being designated as a burr and high proportion of low frequency components being designated as a pit.

Figure 6:
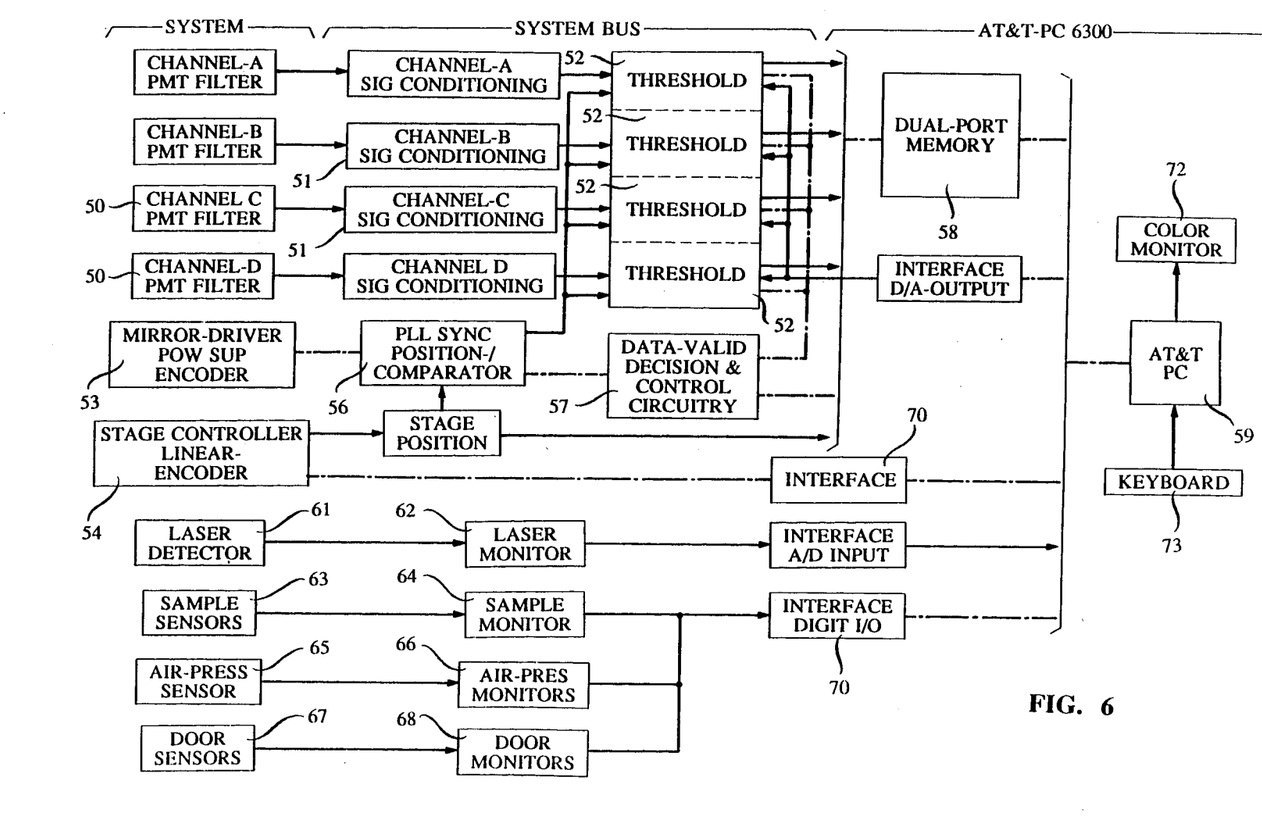
FIG. 6 is an electronic block diagram showing functions of the apparatus of FIG. 3.

An electronic block diagram of the apparatus of FIG. 3 is illustrated in FIG. 6. Each of the photomultiplier tubes 49 of FIG. 3 corresponds to a separate photomultiplier tube (PMT) 50 with a filter. The filter is tuned to the frequency of the helium-neon laser and filters out other ambient light. Each of the PMTs 50 is connected to a signal conditioning circuit 51, the purpose of which is to normalize and amplify the electrical signals. The outputs of the signal conditioning circuits are directed to threshold detectors 52. Each of the defects to be detected results in a burst or pulse of scattered light detected by the appropriately placed optical fibers. The detectors 52 define a threshold by information stored in the computer and record a response only to those pulses that have a height and a width that exceeds the stored threshold. The defect pulse is then converted to a digital representation of its height and width, and thus can be processed by the computer apparatus.

A mirror-driver power supply encoder 53 is an encoder mounted on a rotating shaft of the mirror 38, and it generates a signal indicative of the position of the scanning laser beam on the substrate surface. Likewise, a stage controller linear-encoder 54 generates a signal describing the position in the y direction of the stage supporting the substrate. These signals are combined in a phase-locked loop 56 which in turn transmits information to control circuitry 57. Control circuitry 57 may be programmed to screen out all signals originating from certain locations on the substrate surface, which is useful if only certain "window" portions of the substrate surface are to be inspected. This screening is done by the control circuitry 57 based on information stored in a dual-port memory 58. The control circuitry 54 and the analog to digital conversion circuits 52 are connected to the dual-port memory 58 which accommodates a very high speed of input and interface with a computer 59. The dual-port memory 58 provides information to computer 59 at an appropriate speed for its operation.

A laser detector 61, together with control circuitry 62, monitors the power output of laser 36. A sample sensor 63 and control circuitry 64 detect the presence of the substrate 30 in the support carriage. Prior to inspection, an air jet (not shown) is used to clear the surface of the substrate of dust particles. An air pressure sensor 65 and control circuitry 66 monitors the air pressure constituting the air jet. A door sensor 67 and control circuitry 68 are used for safety purposes to prevent operation if an operator's hand is near the system.

Interface circuits 70 couple these sensor circuits to the computer 59. The computer 59 is connected to a color monitor 72 for giving a visual indication of imperfections and to a keyboard 73 for providing input information.

It is often desirable to use the invention for inspecting ceramic substrates upon which circuit patterns have already been formed. High density circuit patterns typically used in modern hybrid integrated circuits have conductors that are sufficiently close together to diffract the light of the scanning laser beam. We have found that this diffracted light is best separated from the desired scattered light by arranging the substrate such that the laser beam scans the regular pattern at about a 45 degree angle. We have found that under that condition the angle with respect to the normal of diffracted light is a minimum, and therefore inherently separated from the desired scattered light which is always at a high angle with respect to the surface normal.

Figure 7:
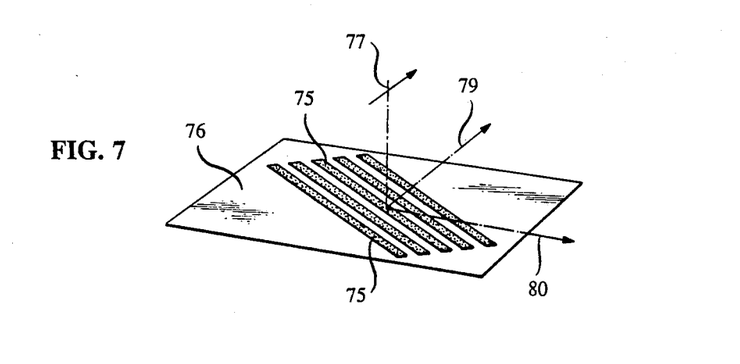
FIG. 7 illustrates diffraction resulting from laser scanning of a regular pattern on a flat surface.

This is illustrated in FIG. 7 in which conductors 75 located on the surface of a ceramic substrate 76 are arranged to be at a 45 degree angle with respect to the direction of scan of the laser beam 77. Under this condition, the light 79 diffracted by the conductive pattern will be in a direction perpendicular to the axis of the conductor pattern; whereas, light 80, which is received in accordance with the invention, is scattered at a other angles with respect to the direction of the diffracting surface.

While the invention has been described as a method for inspecting the surfaces of ceramic substrates, it is apparent that the principles of the invention may be applied to the inspection of any flat surface, including metal surfaces. Particularly, it may be useful for inspecting flat surfaces of photolithographic masks, which must normally be free of minor surface imperfections. The details of the specific embodiment described for inspecting alumina substrates should not be construed as being essential and should not limit the invention. Various other embodiments and modifications of the invention may be devised without departing from the spirit and scope of the invention.

What is claimed is:

1. A method for detecting defects on a flat surface comprising the steps of scanning the surface with a laser beam, receiving light scattered from the surface at a large angle with respect to the surface normal, and comparing the reception of pulses of scattered light that exceed a threshold value with the location of the scanning beam at the time of the reception of such pulses to determine the location of a defect characterized by:

independently receiving first light scattered predominantly only in a first direction from the flat surface; independently receiving second light scattered predominantly only in a second direction significantly different for the first direction from the flat surface; using the location of the scanning beam during the reception of any first light in the form of a pulse that exceeds a threshold value to determine the size in a first dimension of a defect causing the light pulse; and using the location of the scanning beam during the reception of any second light in the form of a pulse that exceeds a threshold to determine the size in a second dimension of a defect causing the light pulse.

2. The method in claim 1 further characterized in that:
the light received by the first and second light guides is scattered at a very high angle of more than about 80 degrees with respect to a normal to the surface.

3. The method of claim 2 further characterized in that:
the second direction is substantially orthogonal to the first direction;
the first light guides are arranged in a first row along a first edge of the planar surface; and the second light guides are arranged in a second row along a second edge of the planar surface which is substantially orthogonal to the first row.

4. The method of claim 3 further characterized by:
using the output of the first row of light guides to determine the length in the second direction of any defect on the planar surface, and using the output of the second row of light guides to determine the length in the first direction of any defect on the planar surface.

5. The method of claim 4 further characterized by:
detecting the Fourier frequency content of light scattered by defects; determining whether such frequency content contains a relatively large quantity of high frequencies or a relative large quantity of low frequencies; and designating those with a high frequency content as burrs and those with a low frequency content as pits.

6. The method of claim 3 further characterized in that third light guides are arranged in a third row along a third edge of the planar surface substantially parallel to the first row; fourth light guides are arranged in a fourth row along a fourth edge of the planar surface substantially parallel to the second row; the third light guides are connected to a third detector arranged to convert to electrical information light scattered from the surface in a third direction substantially opposite the first direction; the fourth light guides are connected to a fourth detector arranged to convert to electrical information light scattered from the surface in a fourth direction substantially opposite the second direction; information from the third and fourth detectors is separately channeled to the computer; and the computer is used to compare separate information from the third detector with third stored information and information from the fourth detector with fourth stored information.

7. The method of claim 6 further characterized by:
combining information from the four detectors with information describing the location of the laser beam scan to determine the dimensions of any defect or particle detected.

8. The method of claim 7 further characterized by:
determining whether light is first scattered by a defect in the direction of beam scan or opposite the direction of beam scan; and using that determination to designate the defect as a pit or a burr.

9. The method of claim 8 further characterized in that the flat surface is a surface of a ceramic substrate.

10. A method for detecting small defects or particles on a surface comprising the steps of arranging a plurality of light guides near the periphery of the surface, scanning the surface with a laser beam, and analyzing light scattered from the surface and received by the light guides characterized in that:
the laser beam raster scans the surface in a first direction; first light guides are connected to a first detector arranged to convert to electrical information light scattered from the surface in the first direction; second light guides are connected to a second detector arranged to convert to electrical information light scattered from the surface in a second direction substantially orthogonal to the first direction; information from the first and second detectors is separately channeled to a computer; and the computer is used to compare separate information from the first detector with first stored information and information from the second detector with second stored information.

11. The method of claim 10 further characterized in that a first and second light guides are positioned so as to receive light scattered at a very high angle of more than about 80 degrees with respect to a normal to the surface;
the first light guides are arranged in a first row along a first edge of the surface; and the second light guides are arranged in a second row along a second edge of the surface substantially orthogonal to the first row.

12. The method of claim 11 further characterized by using the output of the first detector to determine the dimension in the second direction of any defect on the surface; and using the output of the second detector to determine the dimension in the first direction of any defect on the surface.

13. The method of claim 10 further characterized in that
the ends of the fibers that receive the scattered light are located along an edge of the flat surface so as to receive light scattered at a high angle with respect to the surface normal; determining which scattered light received by the optical fibers exceeds a threshold value; comparing the location of the optic fibers that receives light exceeding the threshold value with the position of the scanning laser beam on the flat surface at the time of such reception to determine the dimensions and location of a defect on the surface.

14. A method for detecting small defects or particles on a flat surface comprising the steps of arranging a plurality of optical fibers near the periphery of the surface such that one end of each fiber is capable of receiving light scattered from the surface, scanning the surface with a laser beam, and analyzing light scattered from the surface at a high angle with respect to surface normal and received by the optical fibers characterized in that
the optical fibers are arranged in first, second, third and fourth arrays around the surface periphery, each fiber of each array extending in substantially the same direction; the first and third arrays being arranged on opposite sides of the surface and being substantially parallel; the second and fourth arrays being arranged in opposite sides of the surface, being substantially mutually parallel, and being orthogonal to the first and third arrays; the first, second, third and fourth arrays being respectively connected to first, second, third and fourth detectors; and information from the first, second, third and fourth detectors is separately analyzed with respect to the position of the scanning laser beam to determine the dimensions of any defect or particle.

15. The method of claim 14 further characterized by: determing whether light is first scattered by a defect in the direction of laser beam scan or opposite the direction of laser beam scan; and designating those defects in which light is first scattered in the direction beam scan as a pit and those defects in which light is first scattered opposite the direction of beam scan as a pit.

16. The method of claim 14 wherein the flat surface is a substrate surface containing a plurality of substantially parallel conductors extending predominantly in a first direction characterized by arranging the substrate with respect to the scanning laser beam such that the beam scans the surface at substantially a 45 degree angle with respect to the first direction.

* * * * *

UNITED STATES PATENT AND TRADEMARK OFFICE
CERTIFICATE OF CORRECTION

PATENT NO. : 4,849,645

DATED : July 18, 1989

INVENTOR(S) : Barry J. Mendenko and Bruce M. Nyman

It is certified that error appears in the above—identified patent and that said Letters Patent is hereby corrected as shown below:

Column 7, Line 5, "for" should read --from--.

Column 8, Line 29, "a" should read --the--.

Signed and Sealed this

Twelfth Day of June, 1990

Attest:

HARRY F. MANBECK, JR.

*Attesting Officer*  *Commissioner of Patents and Trademarks*